(12) United States Patent
Chiel et al.

(10) Patent No.: US 11,065,467 B2
(45) Date of Patent: Jul. 20, 2021

(54) SYSTEMS AND METHODS FOR FAST AND REVERSIBLE NERVE BLOCK

(71) Applicant: Case Western Reserve University, Cleveland, OH (US)

(72) Inventors: Hillel Chiel, Cleveland, OH (US);
Niloy Bhadra, Cleveland, OH (US);
Mike Jenkins, Cleveland, OH (US);
Emilie Lothet, Cleveland, OH (US);
Tina Vrabec, Cleveland, OH (US);
Kevin Kilgore, Cleveland, OH (US);
Narendra Bhadra, Cleveland, OH (US); Eric Duco Jansen, Cleveland, OH (US)

(73) Assignees: CASE WESTERN RESERVE UNIVERSITY, Cleveland, OH (US);
VANDERBILT UNIVERSITY, Nashville, TN (US)

( * ) Notice: Subject to any disclaimer, the term of this patent is extended or adjusted under 35 U.S.C. 154(b) by 248 days.

(21) Appl. No.: 16/296,617

(22) Filed: Mar. 8, 2019

(65) Prior Publication Data
US 2019/0201703 A1    Jul. 4, 2019

Related U.S. Application Data

(62) Division of application No. 16/159,748, filed on Oct. 15, 2018, now Pat. No. 10,322,293, which is a
(Continued)

(51) Int. Cl.
*A61N 1/40* (2006.01)
*A61N 5/06* (2006.01)
(Continued)

(52) U.S. Cl.
CPC .............. *A61N 1/403* (2013.01); *A61F 7/007* (2013.01); *A61N 1/06* (2013.01); *A61N 1/28* (2013.01);
(Continued)

(58) Field of Classification Search
CPC .. A61N 1/403; A61N 1/36167; A61N 5/0622; A61N 5/0625; A61N 7/02;
(Continued)

(56) References Cited

U.S. PATENT DOCUMENTS

| 2009/0149926 A1 | 6/2009 | Dacey, Jr. et al. |
| 2011/0092880 A1 | 4/2011 | Gertner |
| 2013/0184636 A1 | 7/2013 | Creasey |

FOREIGN PATENT DOCUMENTS

| WO | 2009/058268 A1 | 5/2009 |
| WO | 2009/073208 A1 | 6/2009 |

(Continued)

OTHER PUBLICATIONS

Abaya, T. V. F., et al. "Characterization of a 3D optrode array for infrared neural stimulation." Biomedical optics express 3.9 (2012): 2200-2219.

(Continued)

*Primary Examiner* — Bo Joseph Peng
(74) *Attorney, Agent, or Firm* — Tarolli, Sundheim, Covell & Tummino LLP

(57) ABSTRACT

One aspect of the present disclosure relates a system that can quickly and reversibly block conduction in a nerve. The system can include a first nerve block modality that provides heat to the nerve to block conduction in the nerve. For example, the heat can provide the quick nerve block. The system can also include a second nerve block modality that provides an electrical signal to the nerve to block the conduction in the nerve. For example, the electrical signal
(Continued)

can provide the reversibility. In some instances, the heat can be provided by an infrared light signal and the electrical signal can be provided by a kilohertz frequency alternating current (KHFAC) signal or a direct current (DC) signal.

5 Claims, 10 Drawing Sheets

Related U.S. Application Data division of application No. 15/126,610, filed as application No. PCT/US2015/020951 on Mar. 17, 2015, now Pat. No. 10,758,738.

(60) Provisional application No. 61/954,915, filed on Mar. 18, 2014.

(51) Int. Cl.
*A61N 7/02* (2006.01)
*A61N 1/06* (2006.01)
*A61N 1/28* (2006.01)
*A61N 1/36* (2006.01)
*A61F 7/00* (2006.01)
A61N 5/067 (2006.01)
A61N 7/00 (2006.01)

(52) U.S. Cl.
CPC ..... *A61N 1/36067* (2013.01); *A61N 1/36071* (2013.01); *A61N 1/36167* (2013.01); *A61N 5/0622* (2013.01); *A61N 5/0625* (2013.01); *A61N 7/02* (2013.01); A61F 2007/0071 (2013.01); A61N 2005/067 (2013.01); A61N 2005/0659 (2013.01); A61N 2007/0021 (2013.01)

(58) Field of Classification Search
CPC ........ A61N 1/06; A61N 1/28; A61N 1/36067; A61N 1/36071; A61N 2005/067; A61N 2007/0021; A61N 2005/0659; A61F 7/007; A61F 2007/0071
See application file for complete search history.

(56) References Cited

FOREIGN PATENT DOCUMENTS

WO 2009/075783 A1 6/2009
WO 2013/188753 A1 12/2013

OTHER PUBLICATIONS

Abel, Na, Smith RA (1994) Intrathecal baclofen for the treatment of intractable spasticity. Arch Phys Med Rehabil. 75:54-58.
Ackermann Jr, D. Michael, et al. "Conduction block of peripheral nerve using high-frequency alternating currents delivered through an intrafascicular electrode." Muscle & Nerve: Official Journal of the American Association of Electrodiagnostic Medicine 41.1 (2010): 117-119.
Ackermann Jr, D. Michael, et al. "Electrical conduction block in large nerves: high-frequency current delivery in the nonhuman primate." Muscle & nerve 43.6 (2011): 897-899.
Ackermann Jr, D. Michael, et al. "Separated interface nerve electrode prevents direct current induced nerve damage." Journal of neuroscience methods 201.1 (2011): 173-176.
Ackermann Jr, Douglas Michael. Reduction of the onset response in high frequency nerve block. Diss. Case Western Reserve University, 2010.
Ackermann, D. Michael, et al. "Conduction block of whole nerve without onset firing using combined high frequency and direct current." Medical & biological engineering & computing 49.2 (2011): 241-251.
Ackermann, D. Michael, et al. "Dynamics and sensitivity analysis of high-frequency conduction block." Journal of neural engineering 8.6 (2011): 065007.
Ackermann, D. Michael, et al. "Effect of bipolar cuff electrode design on block thresholds in high-frequency electrical neural conduction block." IEEE Transactions on Neural Systems and Rehabilitation Engineering 17.5 (2009): 469.
Ackermann, D. Michael, et al. "Effect of nerve cuff electrode geometry on onset response firing in high-frequency nerve conduction block." IEEE Transactions on Neural Systems and Rehabilitation Engineering 18.6 (2010): 658-665.
Ackermann, D. Michael, et al. "Electrode design for high frequency block: effect of bipolar separation on block thresholds and the onset response." Engineering in Medicine and Biology Society, 2009. EMBC 2009. Annual International Conference of the IEEE. IEEE, 2009.
Ackermann, D. Michael, et al. "Nerve conduction block using combined thermoelectric cooling and high frequency electrical stimulation." Journal of neuroscience methods 193.1 (2010): 72-76.
Adamczyk, Margaret Marie, and Patrick E. Crago. "Input-output nonlinearities and time delays increase tracking errors in hand grasp neuroprostheses." IEEE Transactions on Rehabilitation Engineering 4.4 (1996): 271-279.
Adams, Melanie M., and Audrey L. Hicks. "Spasticity after spinal cord injury." Spinal cord 43.10 (2005): 577.
Al-Khodairy, A. T., C. Gobelet, and A. B. Rossier. "Has botulinum toxin type A a place in the treatment of spasticity in spinal cord injury patients?." Spinal cord 36.12 (1998): 854.
Andreani, Juan Carlos M., and Cristina Guma. "New Animal Model to Mimic Spastic Cerebral Palsy: The Brain Damaged Pig Preparation." Neuromodulation: Technology at the Neural Interface 11.3 (2008): 196-201.
Azizi, Farouk, et al. "Chemical neurostimulation using pulse code modulation (PCM) microfluidic chips." Journal of neuroscience methods 192.2 (2010): 193-198.
Bhadra, Narendra, et al. "High frequency electrical conduction block of the pudendal nerve." Journal of neural engineering 3.2 (2006): 180.
Bhadra, Narendra, et al. "Urethral pressure profiles in the female canine implanted with sacral anterior nerve root electrodes." World journal of urology 19.4 (2001): 272-277.
Bhadra, Niloy, et al. "Implementation of an implantable joint-angle transducer." Journal of rehabilitation research and development 39.3 (2002): 411-422.
Bhadra, Niloy, et al. "Reduction of the onset response in high frequency nerve block with amplitude ramps from non-zero amplitudes." Engineering in Medicine and Biology Society, 2009. EMBC 2009. Annual International Conference of the IEEE. IEEE, 2009.
Bhadra, Niloy, et al. "Simulation of high-frequency sinusoidal electrical block of mammalian myelinated axons." Journal of computational neuroscience 22.3 (2007): 313-326.
Bharda, Niloy, and Kevin L. Kilgore. "Direct current electrical conduction block of peripheral nerve." IEEE Transactions on Neural Systems and Rehabilitation Engineering 12.3 (2004): 313-324.
Bharda, Niloy, and Kevin L. Kilgore. "High-frequency electrical conduction block of mammalian peripheral motor nerve." Muscle & Nerve: Official Journal of the American Association of Electrodiagnostic Medicine 32.6 (2005): 782-790.
Boger, Adam S., Narendra Bhadra, and Kenneth J. Gustafson. "High frequency sacral root nerve block allows bladder voiding." Neurourology and urodynamics 31.5 (2012): 677-682.
Boger, Adam, Narendra Bhadra, and Kenneth J. Gustafson. "Bladder voiding by combined high frequency electrical pudendal nerve block and sacral root stimulation." Neurourology and Urodynamics: Official Journal of the International Continence Society 27.5 (2008): 435-439.
Bowman, Bruce R., and Donald R. McNeal. "Response of single alpha motoneurons to high-frequency pulse trains." Stereotactic and Functional Neurosurgery 49.3 (1986): 121-138.

(56) References Cited

OTHER PUBLICATIONS

Cayce, Jonathan M., et al. "Infrared neural stimulation of primary visual cortex in non-human primates." Neuroimage 84 (2014): 181-190.

Cayce, Jonathan M., et al. "Infrared neural stimulation of thalamocortical brain slices." IEEE Journal of Selected Topics in Quantum Electronics 16.3 (2010): 565-572.

Cayce, Jonathan M., et al. "Pulsed infrared light alters neural activity in rat somatosensory cortex in vivo." Neuroimage 57.1 (2011): 155-166.

Chernov, Mykyta M., et al. "Material considerations for optical interfacing to the nervous system." MRS bulletin 37.6 (2012): 599-605.

Choen, Mark L., and Zhanna Georgievskaya. "Histopathology of the stimulated vagus nerve: primum non nocere." Heart failure reviews 16.2 (2011): 163-169.

Coffey, Robert J., et al. "Abrupt withdrawal from intrathecal baclofen: recognition and management of a potentially life-threatening syndrome." Archives of physical medicine and rehabilitation 83.6 (2002): 735-741.

Corning ClearCurve Optical Fiber Specification Sheets printed from http://www.corning.com/opticalfiber/products/clearcurve/single_mode_fiber.aspx, accessed Apr. 11, 2017.

Cullins, Miranda J., and Hillel J. Chiel. "Electrode fabrication and implantation in Aplysia californica for multi-channel neural and muscular recordings in intact, freely behaving animals." Journal of visualized experiments: JoVE 40 (2010).

Damiano, Diane L., Katharine E. Alter, and Henry Chambers. "New clinical and research trends in lower extremity management for ambulatory children with cerebral palsy." Physical Medicine and Rehabilitation Clinics 20.3 (2009): 469-491.

Delgado, Mauricio R., et al. "Practice parameter: pharmacologic treatment of spasticity in children and adolescents with cerebral palsy (an evidence-based review): report of the Quality Standards Subcommittee of the American Academy of Neurology and the Practice Committee of the Child Neurology Society." Neurology 74.4 (2010): 336-343.

Dimarco, Anthony F., and Krzysztof E. Kowalski. "Activation of inspiratory muscles via spinal cord stimulation." Respiratory physiology & neurobiology 189.2 (2013): 438-449.

Dittami, Gregory M., et al. "Intracellular calcium transients evoked by pulsed infrared radiation in neonatal cardiomyocytes." The Journal of physiology 589.6 (2011): 1295-1306.

Duke, Austin R., et al. "Combined optical and electrical stimulation of neural tissue in vivo." Journal of biomedical optics 14.6 (2009): 060501.

Duke, Austin R., et al. "Hybrid electro-optical stimulation of the rat sciatic nerve induces force generation in the plantarflexor muscles." Journal of neural engineering 9.6 (2012): 066006.

Duke, Austin R., et al. "Spatial and temporal variability in response to hybrid electro-optical stimulation." Journal of neural engineering 9.3 (2012): 036003.

Duke, Austin R., et al. "Transient and selective suppression of neural activity with infrared light." Scientific reports 3 (2013): 2600.

Durfee, W. K., T. R. Mariano, and J. L. Zahradnik. "Simulator for evaluating shoulder motion as a command source for FES grasp restoration systems." Archives of physical medicine and rehabilitation 72.13 (1991): 1088-1094.

Feng, Hua-Jun, et al. "Alteration of GABAergic neurotransmission by pulsed infrared laser stimulation." Journal of neuroscience methods 192.1 (2010): 110-114.

Flett, Peter J. "Rehabilitation of spasticity and related problems in childhood cerebral palsy." Journal of Paediatrics and child health 39.1 (2003): 6-14.

Foldes, Emily L., et al. "Counted cycles method to quantify the onset response in high-frequency peripheral nerve block." Engineering in Medicine and Biology Society, 2009. EMBC 2009. Annual International Conference of the IEEE. IEEE, 2009.

Foldes, Emily L., et al. "Design, fabrication and evaluation of a conforming circumpolar peripheral cuff nerve cuff electrode for acute experimental use." Journal of neuroscience methods 196.1 (2011): 31-37.

Franke, Manfred, et al. "Chronic bladder control post SCI via Electric Pudendal Nerve Block."

Fried, Nathaniel M., et al. "Noncontact stimulation of the cavernous nerves in the rat prostate using a tunable-wavelength thulium fiber laser." Journal of endourology 22.3 (2008): 409-414.

Fu, Xiaoyong, et al. "Fiber-optic catheter-based polarization-sensitive OCT for radio-frequency ablation monitoring." Optics letters 39.17 (2014): 5066-5069.

Gaunt, Robert A., and Arthur Prochazka. "Transcutaneously coupled, high-frequency electrical stimulation of the pudendal nerve blocks external urethral sphincter contractions." Neurorehabilitation and neural repair 23.6 (2009): 615-626.

Gerges, Meana, et al. "Frequency-and amplitude-transitioned waveforms mitigate the onset response in high-frequency nerve block." Journal of neural engineering 7.6 (2010): 066003.

Goyal, Vinay, et al. "Acute damage threshold for infrared neural stimulation of the cochlea: functional and histological evaluation." The Anatomical Record: Advances in Integrative Anatomy and Evolutionary Biology 295.11 (2012): 1987-1999.

Gracies, Jean-Michel, et al. "Traditional pharmacological treatments for spasticity part II: general and regional treatments." Muscle & Nerve: Official Journal of the American Association of Electrodiagnostic Medicine 20.S6 (1997): 92-120.

Grill, Warren M., and J. Thomas Mortimer. "Neural and connective tissue response to long-term implantation of multiple contact nerve cuff electrodes." Journal of Biomedical Materials Research: An Official Journal of The Society for Biomaterials, The Japanese Society for Biomaterials, and The Australian Society for Biomaterials and the Korean Society for Biomaterials 50.2 (2000): 215-226.

Halpern, Jeffrey M., et al. "Diamond electrodes for neurodynamic studies in Aplysia californica." Diamond and related materials 15.2-3 (2006): 183-187.

Hansen, Colby R., Judith L. Gooch, and Teresa Such-Neibar. "Prolonged, severe intrathecal baclofen withdrawal syndrome: a case report." Archives of physical medicine and rehabilitation 88.11 (2007): 1468-1471.

Hines, A. E., P. E. Crago, and C. Billian. "Functional electrical stimulation for the reduction of spasticity in the hemiplegic hand." Biomedical sciences instrumentation 29 (1993): 259-266.

Hodgkin, A. L., and B. Katz. "The effect of temperature on the electrical activity of the giant axon of the squid." The Journal of physiology 109.1-2 (1949): 240-249.

Huxley, Andrew F. "Ion movements during nerve activity." Annals of the New York Academy of Sciences 81.2 (1959): 221-246.

Izzo, Agnella D., et al. "Laser stimulation of auditory neurons: effect of shorter pulse duration and penetration depth." Biophysical journal 94.8 (2008): 3159-3166.

Izzo, Agnella D., et al. "Laser stimulation of the auditory nerve." Lasers in Surgery and Medicine: The Official Journal of the American Society for Laser Medicine and Surgery 38.8 (2006): 745-753.

Izzo, Agnella D., et al. "Optical parameter variability in laser nerve stimulation: a study of pulse duration, repetition rate, and wavelength." IEEE Transactions on Biomedical Engineering 54.6 (2007): 1108-1114.

Jenkins, Michael W., et al. "Optical pacing of the embryonic heart." Nature photonics 4.9 (2010): 623.

Johnson, Mark William, and P. Hunter Peckham. "An implantable transducer for two-degree-of-freedom joint angle sensing." Engineering in Medicine and Biology Society, 1994. Engineering Advances: New Opportunities for Biomedical Engineers. Proceedings of the 16th Annual International Conference of the IEEE. vol. 1. IEEE, 1994.

Johnston, Michael V., et al. "Models of cerebral palsy: which ones are best?." Journal of child neurology 20.12 (2005): 984-987.

Joseph, Laveeta, and Robert J. Butera. "Unmyelinated aplysia nerves exhibit a nonmonotonic blocking response to high-frequency stimulation." IEEE Transactions on Neural Systems and Rehabilitation Engineering 17.6 (2009): 537-544.

(56) References Cited

OTHER PUBLICATIONS

Kang, Wei, et al. "Endoscopically guided spectral-domain OCT with double-balloon catheters." Optics express 18.16 (2010): 17364-17372.

Kang, Wei, et al. "Motion artifacts associated with in vivo endoscopic OCT images of the esophagus." Optics express 19.21 (2011): 20722-20735.

Kilgore, Kevin L., and N. Bhadra. "Nerve conduction block utilising high-frequency alternating current." Medical and Biological Engineering and Computing 42.3 (2004): 394-406.

Kilgore, Kevin L., and Niloy Bhadra. "Reversible nerve conduction block using kilohertz frequency alternating current." Neuromodulation: Technology at the Neural Interface 17.3 (2014): 242-255.

Kilgore, Kevin L., et al. "An implanted upper-extremity neuroprosthesis using myoelectric control." The Journal of hand surgery 33.4 (2008): 539-550.

Kilgore, Kevin L., et al. "Combined direct current and high frequency nerve block for elimination of the onset response." Engineering in Medicine and Biology Society, 2009. EMBC 2009. Annual International Conference of the IEEE. IEEE, 2009.

Kilgore, Kevin L., et al. "Neuroprosthesis consumers' forum: consumer priorities for research directions." Journal of rehabilitation research and development 38.6 (2001): 655-660.

Lewis, Kelly S., and Wade M. Mueller. "Intrathecal baclofen for severe spasticity secondary to spinal cord injury." Annals of Pharmacotherapy 27.6 (1993): 767-774.

Little, J. W. "Spasticity and associated abnormalities of muscle tonus." Rehabilitation medicine (1998).

Lu, Hui, et al. "Selective extracellular stimulation of individual neurons in ganglia." Journal of neural engineering 5.3 (2008): 287.

Lu, Hui, Jeffrey M. McManus, and Hillel J. Chiel. "Extracellularly identifying motor neurons for a muscle motor pool in Aplysia californica." Journal of visualized experiments: JoVE 73 (2013).

Matic, Agnella Izzo, et al. "Behavioral and electrophysiological responses evoked by chronic infrared neural stimulation of the cochlea." PLoS One 8.3 (2013): e58189.

McCreery, D. B., et al. "A quantitative computer-assisted morphometric analysis of stimulation-induced injury to myelinated fibers in a peripheral nerve." Journal of neuroscience methods 73.2 (1997): 159-168.

McCreery, D. B., et al. "Comparison of neural damage induced by electrical stimulation with faradaic and capacitor electrodes." Annals of biomedical engineering 16.5 (1988): 463-481.

McManus, Jeffrey M., Hui Lu, and Hillel J. Chiel. "An in vitro preparation for eliciting and recording feeding motor programs with physiological movements in Aplysia californica." Journal of visualized experiments: JoVE 70 (2012).

Memberg, W. D., et al. "A transducer to measure isometric elbow moments." Clinical Biomechanics 16.10 (2001): 918-920.

Mi, Yan, et al. "Effects of steep pulsed electric fields (SPEF) on mitochondrial transmembrane potential of human liver cancer cell." Engineering in Medicine and Biology Society, 2007. EMBS 2007. 29th Annual International Conference of the IEEE. IEEE, 2007.

Midha, Meena, and James K. Schmitt. "Epidural spinal cord stimulation for the control of spasticity in spinal cord injury patients lacks long-term efficacy and is not cost-effective." Spinal Cord 36.3 (1998): 190.

Miles, J. D., et al. "Effects of ramped amplitude waveforms on the onset response of high-frequency mammalian nerve block." Journal of neural engineering 4.4 (2007): 390.

Molenaers, Guy, et al. "The use of botulinum toxin A in children with cerebral palsy, with a focus on the lower limb." Journal of children's orthopaedics 4.3 (2010): 183-195.

Moore, L-E_. "Membrane conductance changes in single nodes of Ranvier, measured by laser-induced temperature jump experiments." Biochimica et Biophysica Acta (BBA)-Biomembranes 375.1 (1975): 115-123.

Moore, L. E., J. P. Holt Jr, and B. D. Lindley. "Laser temperature-jump technique for relaxation studies of the ionic conductances in myelinated nerve fibers." Biophysical journal 12.2 (1972): 157.

Mou, Zongxia, et al. "A simulation study of the combined thermoelectric extracellular stimulation of the sciatic nerve of the Xenopus laevis: the localized transient heat block." IEEE Transactions on Biomedical Engineering 59.6 (2012): 1758-1769.

Naples, Gregory G., et al. "A spiral nerve cuff electrode for peripheral nerve stimulation." IEEE transactions on biomedical engineering 35.11 (1988): 905-916.

Novachek, Tom F., and James R. Gage. "Orthopedic management of spasticity in cerebral palsy." Child's Nervous System 23.9 (2007): 1015-1031.

Oliveira, Jorge MA. "Mitochondrial membrane potential and dynamics." Mitochondrial Dysfunction in Neurodegenerative Disorders. Springer, London, 2012. 127-139.

Papavasiliou, Antigone S., et al. "Botulinum toxin treatment in upper limb spasticity: treatment consistency." european journal of paediatric neurology 16.3 (2012): 237-242.

PCT International Search Report for corresponding International Application Serial No. PCT/US2015/020951, dated Jul. 7, 2015, pp. 1-13.

Polasek, Katharine H., et al. "Human nerve stimulation thresholds and selectivity using a multi-contact nerve cuff electrode." IEEE transactions on neural systems and rehabilitation engineering 15.1 (2007): 76-82.

Polasek, Katharine H., et al. "Intraoperative testing of selectivity of spiral nerve cuff electrodes." Neural Engineering, 2005. Conference Proceedings. 2nd International IEEE EMBS Conference on. IEEE, 2005.

Polasek, Katharine H., et al. "Spiral nerve cuff electrodes for an upper extremity neuroprosthesis." Engineering in Medicine and Biology Society, 2006. EMBS'06. 28th Annual International Conference of the IEEE. IEEE, 2006.

Polasek, Katharine H., et al. "Stimulation stability and selectivity of chronically implanted multicontact nerve cuff electrodes in the human upper extremity." IEEE Transactions on Neural Systems and Rehabilitation Engineering 17.5 (2009): 428-437.

Puligopu, Aneel Kumar, and Anirudh Kumar Purohit. "Outcome of selective motor fasciculotomy in the treatment of upper limb spasticity." Journal of pediatric neurosciences 6.Suppl1 (2011): S118.

Rajguru, Suhrud M., et al. "Infrared photostimulation of the crista ampullaris." The Journal of physiology 589.6 (2011): 1283-1294.

Rattay, Frank, and Matthias Aberham. "Modeling axon membranes for functional electrical stimulation." IEEE Transactions on Biomedical Engineering 40.12 (1993): 1201-1209.

Richter, C-P., et al. "Neural stimulation with optical radiation." Laser & photonics reviews 5.1 (2011): 68-80.

Russo, Marc, and Jean-Pierre Van Buyten. "10-kHz high-frequency SCS therapy: a clinical summary." Pain Medicine 16.5 (2015): 934-942.

Schiefer, Matthew A., et al. "Selective activation of the human tibial and common peroneal nerves with a flat interface nerve electrode." Journal of neural engineering 10.5 (2013): 056006.

Schulte-Baukloh, Heinrich, et al. "Botulinum neurotoxin type A in urology: antibodies as a cause of therapy failure." International journal of urology 15.5 (2008): 407-415.

Shaprio, Mikhail G., et al. "Infrared light excites cells by changing their electrical capacitance." Nature communications 3 (2012): 736.

Sheean, Geoffrey. "Botulinum toxin treatment of adult spasticity." Drug Safety 29.1 (2006): 31-48.

Silbereis, John C., et al. "Towards improved animal models of neonatal white matter injury associated with cerebral palsy." Disease models & mechanisms 3.11-12 (2010): 678-688.

Smyth, Matthew D., and Warwick J. Peacock. "The surgical treatment of spasticity." Muscle & Nerve: Official Journal of the American Association of Electrodiagnostic Medicine 23.2 (2000): 153-163.

Stetkarova, Ivana, et al. "Intrathecal baclofen in spinal spasticity: frequency and severity of withdrawal syndrome." Pain physician 18.4 (2015): E633-E641.

Verdam, Froukje J., et al. "An update on less invasive and endoscopic techniques mimicking the effect of bariatric surgery." Journal of obesity 2012 (2012).

(56) References Cited

OTHER PUBLICATIONS

Vrabec, T. B. N., et al. "Non-damaging nerve conduction block using direct current." International Functional Electrical Stimulation Society Conference. 2012.

Warman, Eduardo N., and Hillel J. Chiel. "A new technique for chronic single-unit extracellular recording in freely behaving animals using pipette electrodes." Journal of neuroscience methods 57.2 (1995): 161-169.

Wells, Jonathon D., et al. "Application of infrared light for in vivo neural stimulation." Journal of biomedical optics 10.6 (2005): 064003.

Wells, Jonathon D., et al. "Optically mediated nerve stimulation: Identification of injury thresholds." Lasers in Surgery and Medicine: The Official Journal of the American Society for Laser Medicine and Surgery 39.6 (2007): 513-526.

Wells, Jonathon, et al. "Biophysical mechanisms of transient optical stimulation of peripheral nerve." Biophysical journal 93.7 (2007): 2567-2580.

Wells, Jonathon, et al. "Lasers Stimulate New Techniques in Nerve Studies." Biophotonics International 13.10 (2006): 30.

Wells, Jonathon, et al. "Optical stimulation of neural tissue in vivo." Optics letters 30.5 (2005): 504-506.

Wells, Jonathon, et al. "Pulsed laser versus electrical energy for peripheral nerve stimulation." Journal of neuroscience methods 163.2 (2007): 326-337.

Williamson, Richard P., and Brian J. Andrews. "Localized electrical nerve blocking." IEEE Transactions on Biomedical Engineering 52.3 (2005): 362-370.

Woo, Moon Yo, and B. Campbell. "Asynchronous Firing and Block of Peripheral Nerve Conduction by 20 KC Alternating Current." Bulletin of the Los Angeles Neurological Society 29 (1964): 87.

Yablon, Stuart A., et al. "Formation of neutralizing antibodies in patients receiving botulinum toxin type A for treatment of poststroke spasticity: a pooled-data analysis of three clinical trials." Clinical therapeutics 29.4 (2007): 683-690.

SYSTEMS AND METHODS FOR FAST AND REVERSIBLE NERVE BLOCK

RELATED APPLICATIONS

This application is a Divisional of U.S. patent application Ser. No. 16/159,748, filed Oct. 15, 2018, which is Divisional of U.S. patent application Ser. No. 15/126,610, filed Sep. 16, 2016, which is a U.S. National Stage under 35 USC 371 patent application claiming priority to Serial No. PCT/US2015/020951, filed on Mar. 17, 2015, which claims the benefit of U.S. Provisional Application Ser. No. 61/954,915, filed Mar. 18, 2014, entitled "SYSTEM AND METHOD FOR NERVE CONDUCTION BLOCK." Each of which is hereby incorporated by reference for all purposes.

GOVERNMENT SUPPORT

This invention was made with government support under DMS-101043 awarded by the National Science Foundation, R21-HL-115373, R01-NS-074149, and R01-NS-052407 awarded by the National Institutes of Health, and W811XWH-10-C-0208 awarded by the Department of Defense. The government has certain rights in the invention.

TECHNICAL FIELD

The present disclosure relates generally to systems and methods for fast and reversible nerve block and, more specifically, to systems and methods that can apply a heat signal and an electric signal to the nerve to achieve the fast and reversible block.

BACKGROUND

Patients affected with a neurological disorder are prone to chronic pain or spasmodic muscle contractions. Such chronic pain and spasticity can worsen over time without treatment. Drugs or surgery can block undesirable neural activity; however, drugs have a slow time course and may have undesirable side effects and surgery is usually irreversible. An ideal block would be fast and reversible over extended periods.

Kilohertz high-frequency alternating current (KHFAC) provides a promising new technology that reversibly blocks action potentials while still preserving nerve viability. However, nerve block associated with KHFAC is associated with an onset response, during which the nerve fires rapidly for milliseconds to seconds. The onset response can cause brief, but intense, muscle contractions and pain. To improve the clinical utility of KHFAC, the onset response should be eliminated. Increasing neural temperature can induce block (e.g., due to altered ion channel kinetics) quickly and reversibly.

SUMMARY

The present disclosure relates generally to systems and methods for fast and reversible nerve block and, more specifically, to systems and methods that can apply a heat signal and an electric signal (e.g., a kilohertz high frequency alternating current (KHFAC) signal and/or a direct current (DC) signal) to the nerve to achieve the fast and reversible block.

In one aspect, the present disclosure includes a method for blocking conduction in a nerve quickly and reversibly. A nerve block that induces heating can be applied to block conduction in the nerve. Additionally, an electrical nerve block can also be applied to block the conduction in the nerve.

In another aspect, the present disclosure includes a system that can block nerve conduction quickly and reversibly. The system includes a first nerve block modality that provides heat to the nerve to block the nerve conduction. The system also includes a second nerve block modality that provides an electrical signal to the nerve to block the nerve conduction.

In a further aspect, the present disclosure includes a neuroprosthetic system that can perform a fast and reversible nerve block. The neuroprosthetic system can include an optrode that provides heat to a nerve causing the spasticity to block conduction in the nerve. The neuroprosthetic system can also include an electrode that provides an electrical signal to the nerve to block the conduction in the nerve.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
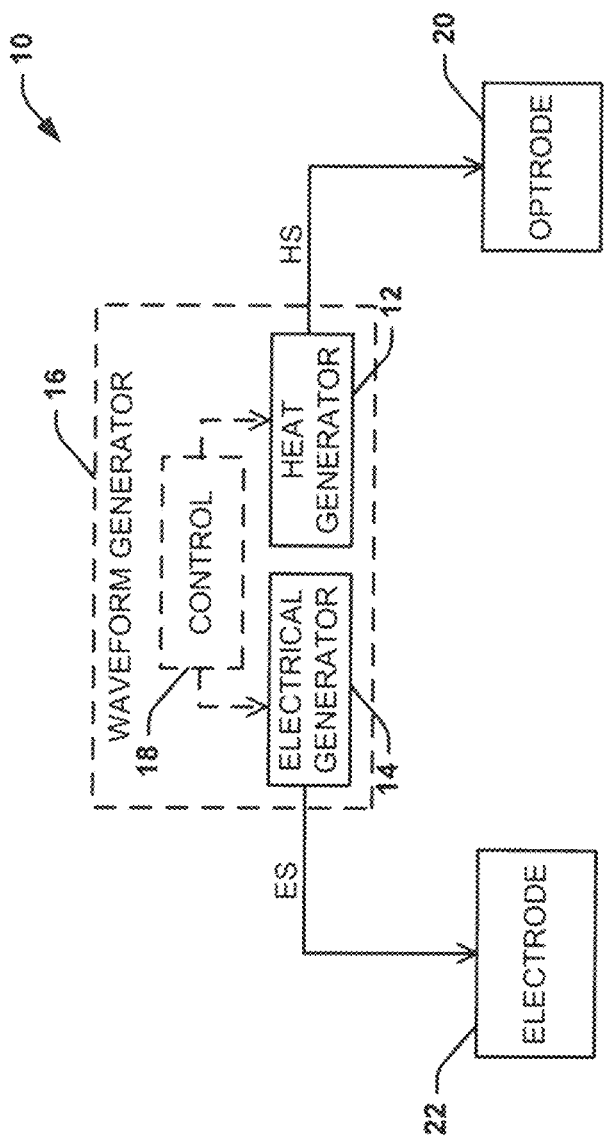
FIG. 1 is a block diagram showing a system for fast and reversible nerve conduction block in accordance with an aspect of the present disclosure.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/ steps) is not limited to the order presented in the claims or figures unless specifically indicated otherwise.

As used herein, the terms "nerve block", "nerve conduction block", and "block" can be used interchangeably when referring to the failure of impulse transmission at some point along a nerve.

As used herein, the terms "substantially blocked" and "substantial block" can interchangeably refer to a complete (e.g., 100%) or partial inhibition (e.g., less than 100%, such as about 90%, about 80%, about 70%, about 60%, or less than about 50%) of nerve conduction through a nerve. When referring to nerve block herein, it will be understood that nerve block can refer to a substantial nerve block.

As used herein, the term "nerve block modality" can refer to a particular mode in which a nerve conduction block can be applied to a nerve of a subject.

One example of a nerve block modality can include heat. The heat can be transmitted to the nerve by a signal that generates heat (a "heat signal") via one or more "optrodes". Such a signal can include an infrared (IR) light signal, a radio frequency (RF) signal, an ultrasound (US) signal, an electrical heating signal, or the like.

Another example of a nerve block modality can include electricity. The electricity can be transmitted to the nerve by an electrical signal via one or more electrodes. Such an electrical signal can include a direct current (DC) signal, an alternating current signal (AC), a high frequency alternating current signal (HFAC), a kilohertz frequency alternating current (KHFAC) signal, or the like.

As used herein, the term "nerve" can refer to one or more fibers that employ electrical and chemical signals to transmit motor, sensory and/or autonomic information from one body part to another. A nerve can refer to either a component of the central nervous system or the peripheral nervous system.

As used herein, the term "neural prosthesis" can refer to one or more devices that can be used to block nerve conduction.

As used herein, the term "onset response" can refer to a finite (e.g., several milliseconds to several seconds) burst of neuronal firing when an electrical signal (e.g., a KHFAC signal for nerve block) is first applied to a nerve.

As used herein, the terms "fast" and "quick" can be used interchangeably when referring to a nerve block that is achieved substantially instantaneously (e.g., in "real-time"). In some instances, the nerve block can be achieved within 1 second. In other instances, the nerve block can be achieved within 500 milliseconds. In still other instances, the nerve block can be achieved within 300 milliseconds. In other instances, the nerve block can be achieved within 100 milliseconds.

As used herein, the term "extended time period" can refer to a time greater than 30 minutes.

As used herein, the term "reversible" can be used to refer to a nerve block that can be applied to substantially block conduction in a nerve and then removed to substantially allow conduction in the nerve. In some instances, the nerve block can be reversed in less than 1 second. In other instances, the nerve block can be reversed in less than 500 ms. In further instances, the nerve block can be reversed in less than 200 ms. In still further instances, the nerve block can be reversed in less than 100 ms.

As used herein, the term "neurological disorder" can refer to a condition or disease characterized at least in part by abnormal conduction in one or more nerves. In some instances, the abnormal conduction can be associated with pain and/or spasticity. Examples of neurological disorders can include stroke, brain injury, spinal cord injury (SCI), cerebral palsy (CP), multiple sclerosis (MS), etc.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

II. Overview

The present disclosure relates generally to systems and methods for fast and reversible nerve block and, more specifically, to systems and methods that can apply a heat signal and an electric signal (e.g., a kilohertz high frequency alternating current (KHFAC) signal and/or a direct current (DC) signal) to the nerve to achieve the fast and reversible block. The block can be delivered repeatedly without damaging neural structures, without altering the conduction properties of the nerve, and without producing systemic side effects.

In some instances, the heat signal can provide the initial block during which the electrical signal can cause spurious conduction due to an onset response. After the onset response (e.g., less than 10 seconds), the heat signal can be turned off and the electrical signal can maintain the block (e.g., for more than 30 minutes). Advantageously, by using the heat signal and the electrical signal, a nearly instant block can be achieved (e.g., within a few milliseconds) without the onset response and maintained for an extended period of time (e.g., more than 30 minutes) without damaging the nerve.

III. Systems

One aspect of the present disclosure, as shown in FIG. 1, includes a system 10 that can provide fast and reversible nerve conduction block. The block can be provided by applying a heat signal (HS) to the nerve by one or more optrodes 20 and an electrical signal (ES) to the nerve by one or more electrodes. By applying the heat signal (HS) and the electrical signal (ES) in combination, the block can be achieved with lower and safer parameters for one or both of the heat signal and/or the electrical signal than either block applied alone. While not wishing to be bound by theory, it is believed that interactions between the heat block and the electrical block can allow the lower and safer block parameters by modulating nerve physiology (e.g., ion channel function). Applying the heat signal (HS) alone for an extended period of time can cause damage to the physiology of the cell so that it cannot be applied repeatedly for an extended period of time without damage. However, it can be applied repeatedly for the quick block of the onset response of the electrical signal (ES). The electrical signal (ES) can provide the maintained block, but suffers from the onset response. Additionally, the electrical signal (ES) can provide an onset response, which can be blocked by the heat signal (HS). Accordingly, the system 10 can provide a fast block, without suffering from the onset response, that provides the block for an extended period of time without damaging the nerve. For example, the block can be achieved in real time (e.g., less than 100 ms). The electrical signal (ES) can provide the prolonged block (e.g., for at least 30 minutes) that is reversible.

In some instances, the system 10 can be employed as part of a neuroprosthetic system (e.g., as part of a conduction block component) to block conduction in a nerve (e.g., to control spasticity in a muscle and/or chronic pain). For example, neuroprosthetic system can provide a user controlled spastic muscle block that can be turned off and on in real time to provide instantaneous control of spasticity.

The system 10 is illustrated schematically as a block diagram with different blocks representing different components. In some instances, the components can include a heat generator 12 operatively coupled to an optrode 20 and an electrical generator 14 operatively coupled to an electrode 22.

The heat generator 12 can generate a heat signal (HS) that can be sent to the optrode 20 for application to a nerve. The optrode 20 can include one or more devices that can deliver the heat signal (HS) to the nerve. The heat signal (HS) can provide the fast block of the conduction in the nerve. For example, upon application of the heat signal (HS), the conduction in the nerve can be blocked within one second or less. In another example, upon application of the heat signal (HS), the conduction in the nerve can be blocked within 500 ms or less. In a further example, upon application of the heat signal (HS), the conduction in the nerve can be blocked within 200 ms or less. In yet another example, upon application of the heat signal (HS), the conduction in the nerve can be blocked within 100 ms or less. Additionally, application of the heat signal (HS) does not result in the spurious nerve activity of an onset response (e.g., caused by the electrical signal (ES)).

In some instances, the heat signal (HS) can include an infrared (IR) light signal, a light signal, a radio frequency (RF) signal, an ultrasound (US) signal, and/or an electrical heating signal. The optrode 20 can include one or more devices that can be used to apply the heat signal (HS) to the nerve. As an example, the optrode 20 can include one or more IR lasers when the heat signal (HS) is an IR light signal. In another example, the optrode can include one or more heating devices when the heat signal (HS) is an electrical heating signal. In a further example, the optrode can include one or more fiber optic devices when the heat signal (HS) is a light signal.

The electrical generator 14 can generate an electrical signal (ES) that can be sent to the electrode 22 for application to the nerve. The electrode 22 can include one or more devices, elements, or components that can apply the electrical signal (ES) to the nerve. In some instances, the electrical signal (ES) can include a direct current (DC) signal, an alternating current (AC) signal, a high frequency alternating current (HFAC) signal, and/or a kilohertz frequency alternating current (KHFAC) signal. The electrical signal (ES) can provide the block for an extended time period. For example, upon application of the electrical signal (ES), the conduction of the nerve can be blocked for 30 minutes or more. The block can be maintained without damaging the neural response, allowing the block to be reversed to enable conduction in the nerve (e.g., within one second or less). However, application of the electrical signal (ES) can evoke an onset response. Accordingly, the heat signal (HS) can be applied to block the evoked onset response.

Figure 3:
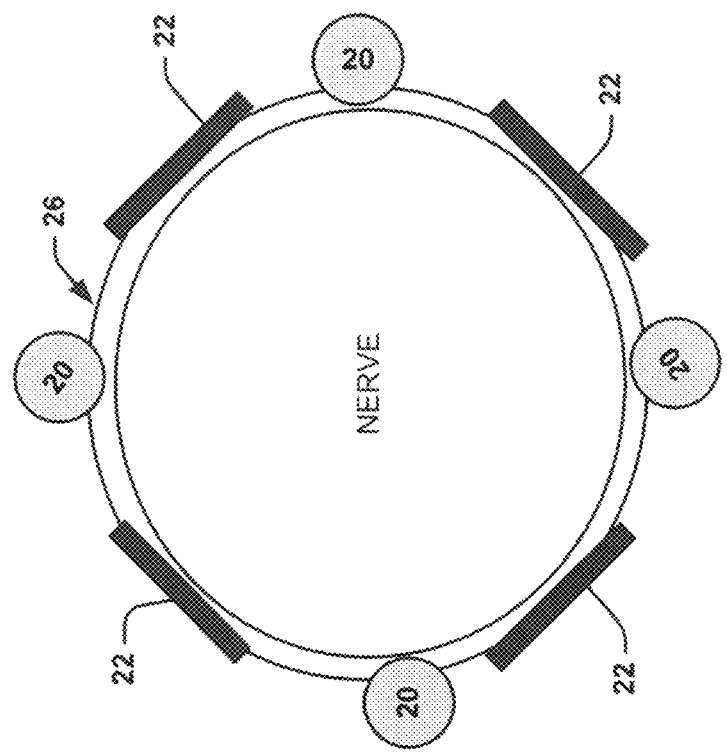
FIGS. 2 and 3 are schematic illustrations showing exemplary configurations of the system in FIG. 1.
Figure 2:
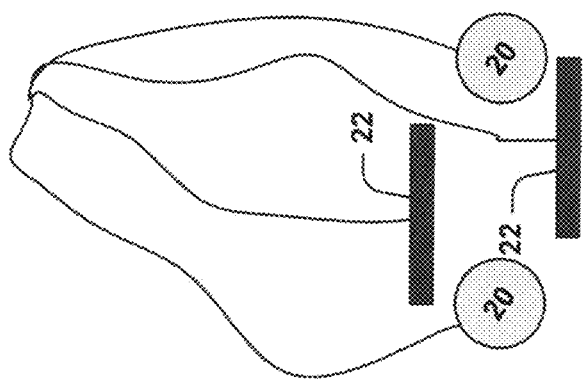

The optrode 20 and the electrode 22 can apply the heat signal (HS) and the electrical signal (ES), respectively, to the nerve. In some instances, as shown in FIG. 2, a plurality of optrodes 20 and a plurality of electrodes 22 can be separate devices, each arranged near the nerve. In other instances, as shown in FIG. 3, the plurality of optrodes 20 and the plurality of electrodes 22 can be combined within a single device, such as a nerve cuff electrode 26. Although two optrodes and two electrodes are illustrated in FIG. 2, and four optrodes and four electrodes are illustrated in FIG. 3, it will be understood that the number of optrodes and electrodes need not be equal, and could be greater or fewer than that illustrated.

Referring again to FIG. 1, in some instances, the heat generator 12 and the electrical generator 14 can be included as part of a waveform generator 16. The waveform generator 16 can include a control device 18 that can regulate the timing, the strength (e.g., amplitude, frequency, etc.), and/or other parameters of the application of the heat signal (HS) and the electrical signal (ES). In some instances, the functions of the control device 18 can be implemented by computer program instructions. These computer program instructions can be stored in a non-transitory memory and provided to a processor of a general purpose computer, special purpose computer, and/or other programmable data processing apparatus to produce a machine, such that the instructions, which execute via the processor of the computer and/or other programmable data processing apparatus, create a mechanism for implementing the functions of the control 18 device specified in the block diagrams.

Figure 4:
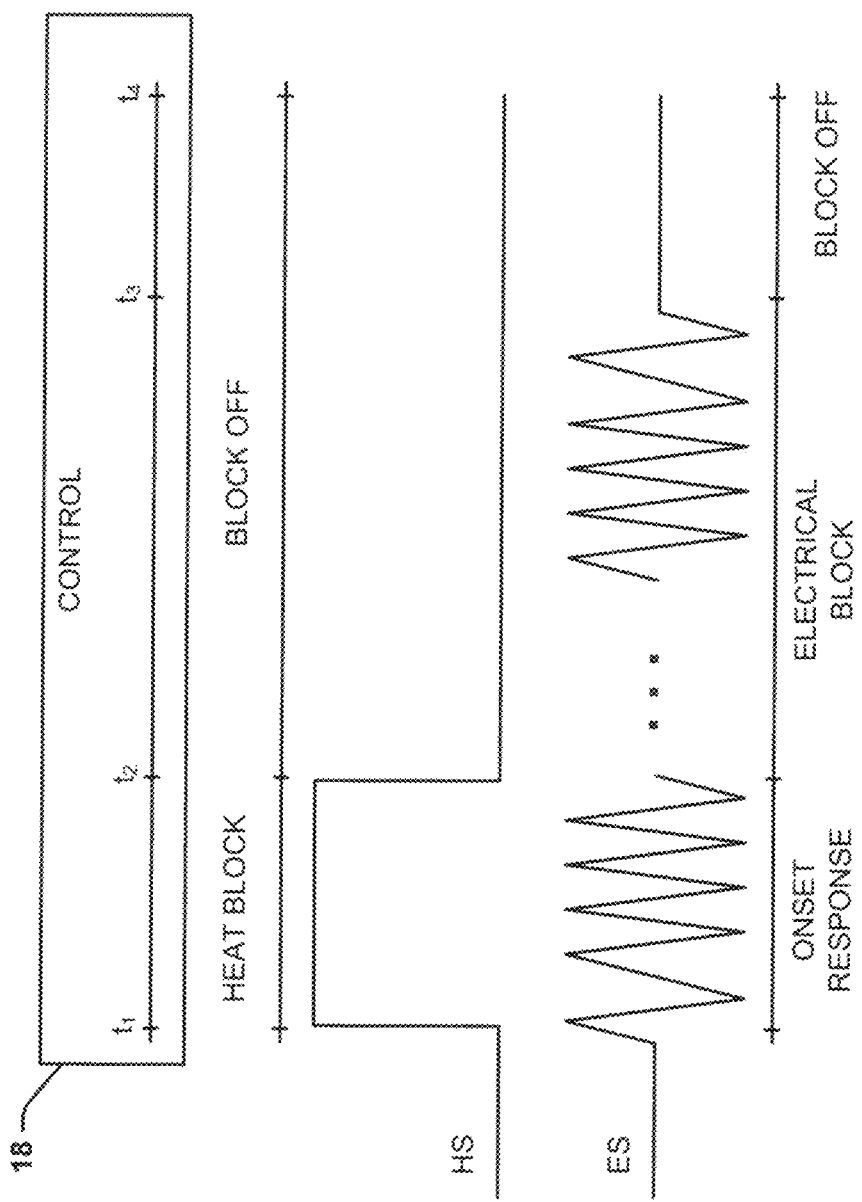
FIGS. 4-6 are schematic depictions of a heat signal and an electrical signal that can be used by the system in FIG. 1 to block nerve conduction.
Figure 5:
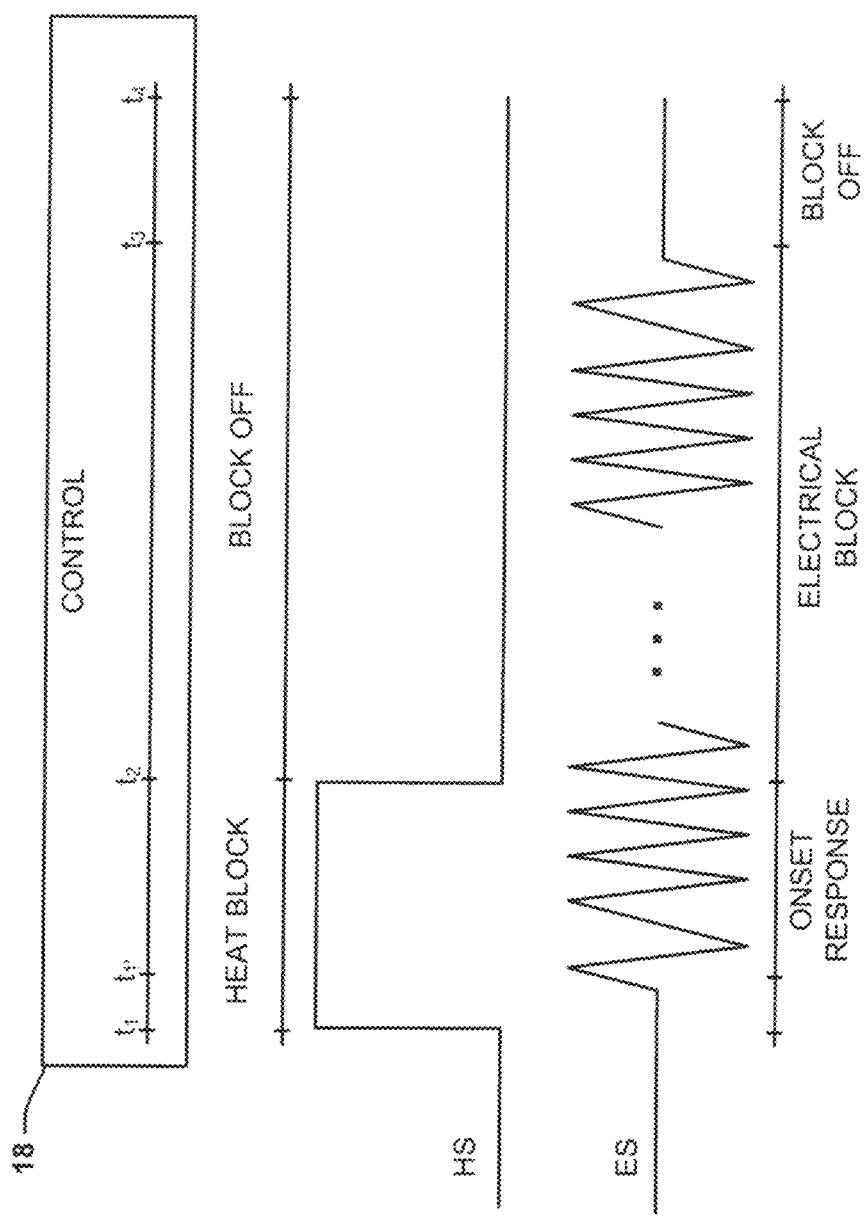
Figure 6:
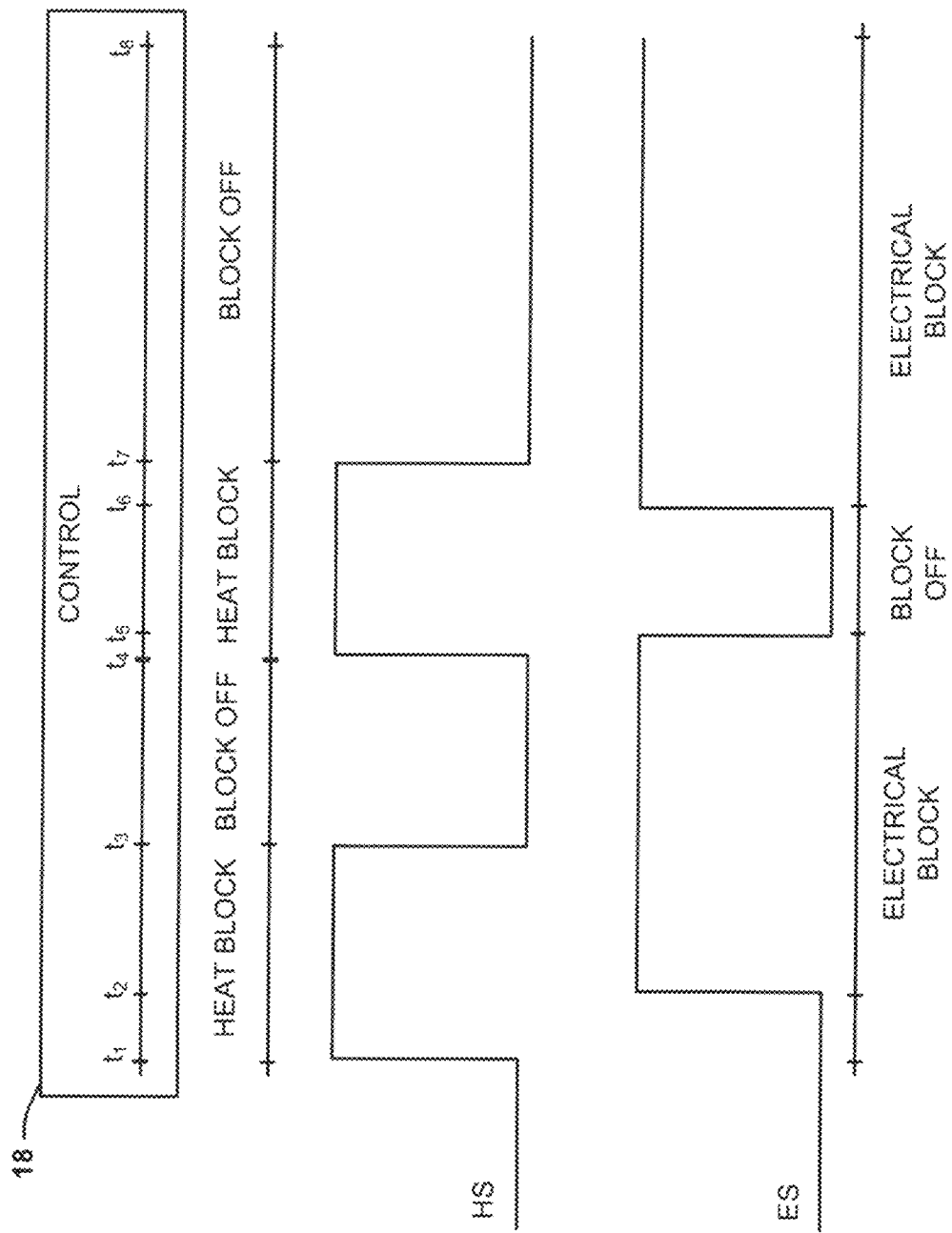

Different examples of timing patterns or functions that can be employed by the control device 18 are shown in FIGS. 4-6. In each case, the heat signal (HS) and the electrical signal (ES) can provide an instant block without the onset response, an extended block without damaging the nerve, a quickly reversible block, and a block that can be delivered repeatedly without damaging neural structures, without altering the conduction properties of the nerve, and without producing systemic side effects. The heat signal (HS) can be applied at least during an onset response generated by the electrical (ES) to block the onset response. For example, the heat signal (HS) can be applied from 1-10 seconds until the onset response resolves. This allows the heat signal (HS) to provide the block without the risk of thermally induced tissue damage. The electrical signal (ES) can provide the block after resolution of the onset response for an extended time period (e.g., at least 30 minutes). Upon removing the block, it is quickly reversible (e.g., allowing conduction in less than 1 second).

In FIG. 4, the heat signal (HS) and the electrical signal (ES) can be applied simultaneously (e.g., both are applied at $t_1$). The electrical signal (ES) can be a KHFAC signal that can provide an onset response that is blocked by the heat signal (HS). The heat signal (HS) can be stopped when the onset response resolves (e.g., at $t_2$). The electrical signal (ES) can provide a block over an extended period of time (e.g., at least 30 minutes). When the electrical signal (ES) is turned off (e.g., at $t_3$), normal function can return to the nerve instantly or almost instantly (e.g., within 1 second). FIG. 5 is similar to FIG. 4, except the electrical signal (ES) is applied slightly after the heat signal (ES) is applied (e.g., at $t_{1'}$). The delay of the electrical signal (ES) with respect to the heat signal (HS) can ensure that the heat signal (HS) has already established the block before the onset response so that the heat signal (HS) is assured of blocking the onset response. FIG. 6 depicts alternating the heat signal (HS) and the electrical signal (ES). As illustrated, the electrical signal (ES) can be a DC signal. As illustrated, the heat signal (HS) and the electrical signal (ES) can overlap in time. Even thought, as illustrated, the amplitudes of the signals remains constant, in some instances, the amplitude of the signals can be sequentially modulated.

IV. Methods

Another aspect of the present disclosure includes methods that can provide fast and reversible nerve conduction block.

Figure 7:
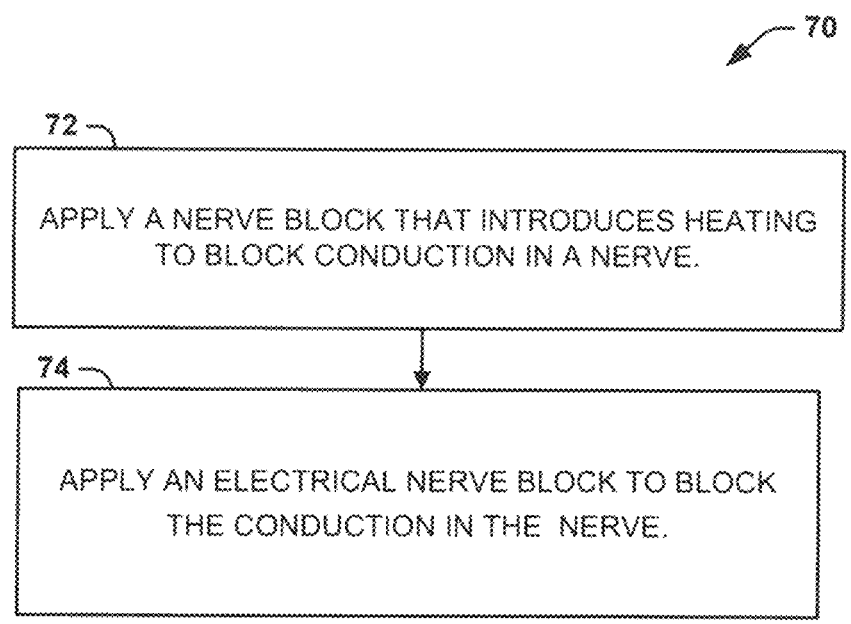
FIG. 7 is a process flow diagram illustrating a method for fast and reversible nerve conduction block according to another aspect of the present disclosure.
Figure 8:
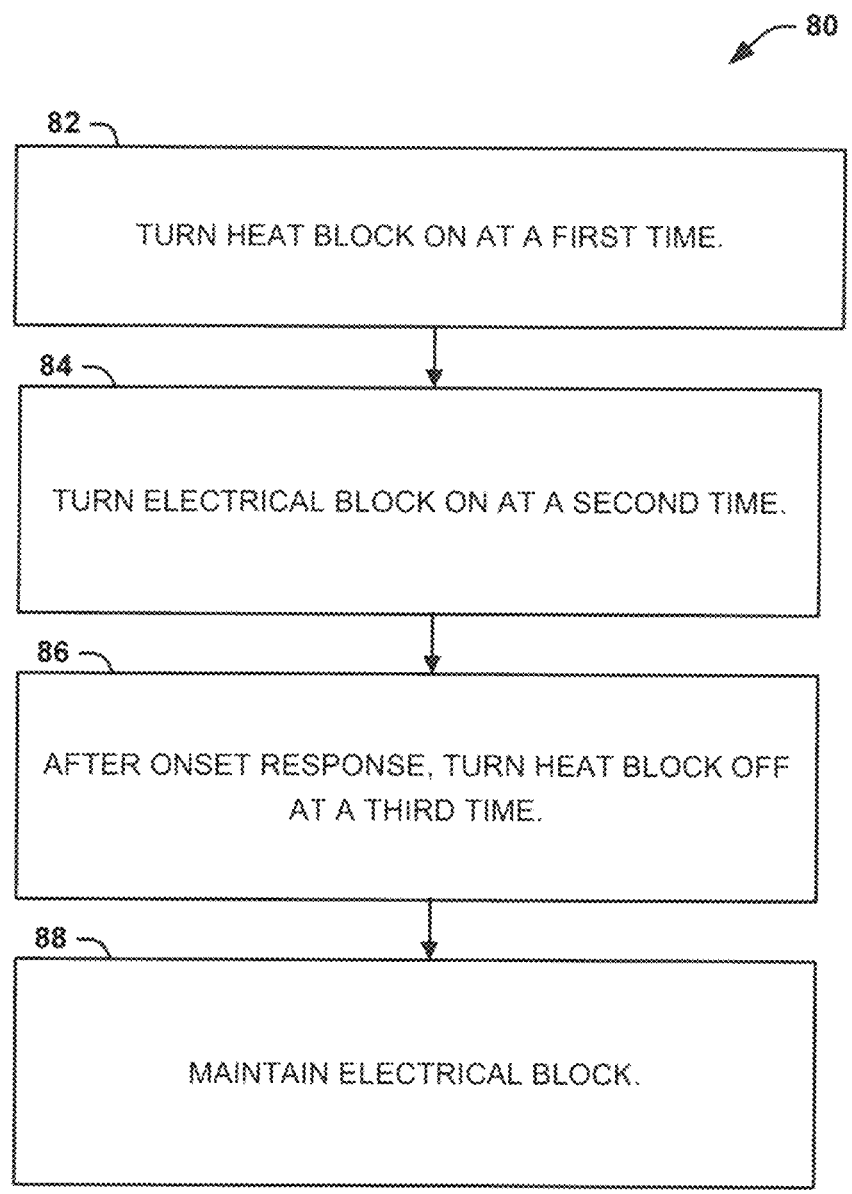
FIG. 8 is a process flow diagram illustrating a method for controlling the nerve conduction block in FIG. 7.

An example of a method 70 that can block the conduction in the nerve is shown in FIG. 7. Another example of a method 80 for controlling the nerve conduction block in FIG. 7 is shown in FIG. 8. The methods 70 and 80 are illustrated as process flow diagrams with flowchart illustrations. For purposes of simplicity, the methods 70 and 80 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 70 and 80.

As shown in FIG. 7, the method 70 can provide fast and reversible nerve conduction block. The method 70 can apply a heat signal and an electrical signal to the nerve to achieve such a block. Indeed, the block can be applied for an extended period of time (e.g., 30 minutes or more) without damaging the nerve, quickly reversible (e.g., within 1 second), and delivered repeatedly without damaging neural structures, without altering the conduction properties of the nerve, and without producing systemic side effects.

At 72, a nerve block that introduces heating (e.g., via a heating signal (HS)) can be applied to a nerve (e.g., via optrode 20) to block conduction in the nerve. At 74, an electrical nerve block (e.g., via an electrical signal (ES)) can be applied to the nerve (e.g., via electrode 22) to block the conduction in the nerve. In some instances, the nerve block that induces heating (e.g., via the heating signal (HS)) can be applied at least during an onset response generated by the electrical nerve block (e.g., via the electrical (ES)) to block the onset response. The electrical nerve block (e.g., via the electrical signal (ES)) can be maintained over an extended time period. The nerve block can be achieved quickly (e.g., within 1 second) and quickly reversible (e.g., within 1 second).

One example of a method 80 for controlling the nerve conduction block in FIG. 7 (e.g., by control 18 device of FIG. 1) is shown in FIG. 8. This example is shown to control the onset response of the electrical signal. In some instances, one or more of the steps of method 80 can be stored in a non-transitory memory device and executed by a processor.

At 82, the heat block can be turned on at a first time. At 84, the electrical block can be turned on at a second time. In one example, the first time and the second time can be equivalent (e.g., as shown in FIG. 4) so that the blocks are applied simultaneously. In another example, the first time and the second time can be different (e.g., as shown in FIG. 5), but the blocks are thereafter applied simultaneously. At 86, after the onset response of the electrical block, the heat block can be tired off at a third time. For example, the nerve block that induces heating can be applied from 1-10 seconds until the onset response resolves. This allows the heat block to provide the block without the risk of thermally induced tissue damage. At 88, the electrical block can be maintained while the heat block is turned off. The electrical block can provide the block after resolution of the onset response for an extended time period (e.g., at least 30 minutes). Upon removing the block, it is quickly reversible (e.g., allowing conduction in less than 1 second).

V. Example

The following example is for the purpose of illustration only and is not intended to limit the scope of the appended claims.

Example

This example demonstrates a fast and reversible nerve block without an onset response using a KHFAC electrical nerve block and an optical nerve block using IR lasers [alternating current and infrared (ACIR)].

Methods

Animal Preparation

Unmyelinated nerves of Aplysia were used. Aplysia can be maintained for many hours and have previously been used to define appropriate parameters for optical block in myelinated rat sciatic nerve Animals 300 to 400 g were used, as their nerves are 4 to 7 cm, with a diameter of 0.5 to 1.5 mm, comparable to rat sciatic nerve. Animals were anesthetized with isotonic magnesium chloride. The pleural-abdominal nerves were maintained in Aplysia saline at room temperature after dissection. All experiments were performed in vitro.

Experimental Setup

Figure 9:
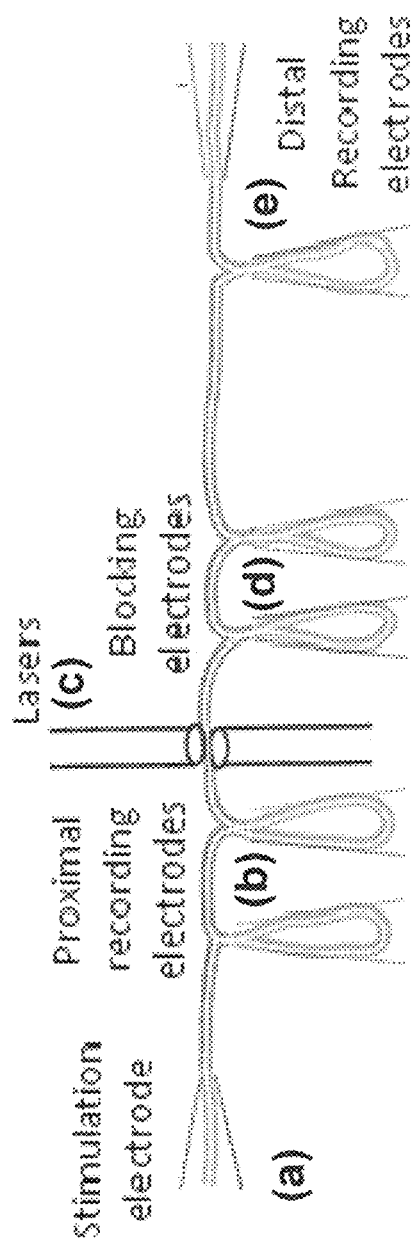
FIG. 9 is a schematic illustration of a nerve preparation incorporating kilohertz high frequency alternating current (KHFAC) and infrared (IR) lasers.

Suction electrodes were placed on the nerve as shown schematically in FIG. 9. A monopolar suction electrode delivered stimulus pulses (a); a pair of en passant electrodes constituted a bipolar proximal recording electrode (b). Two lasers were placed across the nerve (c); a bipolar en passant electrode delivered the KHFAC block (d). A pair of electrodes served as a bipolar distal recording electrode (e). En passant electrodes were chosen for convenience; preliminary data demonstrated that the cuff electrodes could also be used. Each electrode was filled with Aplysia saline solution before suctioning the nerve into the electrode to preserve nerve viability. An Ag/AgCl wire was inserted in each electrode. Electrical stimulation to generate nerve action potentials was controlled by a pulse generator unit (A310 Accupulser, WPI Instruments) via a stimulus isolator (WPI A360, WPI Instruments). KHFAC block was delivered by a controlled constant-current function generator (Keithley 6221) using a sinusoidal waveform. An inductor (8.2 H) was placed across the function generator outputs to minimize DC leakage. The nerve compound action potential (CAP) was monitored using AxoGraph X (AxoGraph Scientific).

Two Capella lasers [Lockheed Martin Aculight, centered at 1860 and 1863 nm and coupled into 600-μm multimode fibers (P600-2-VIS-NIR, Ocean Optics, Dunedin, Fla.)] were placed between the proximal recording and the KHFAC blocking electrodes (e.g., FIG. 9(c)). The small wavelength difference between the lasers was due to different wavelength tuning ranges; water absorption coefficients were similar. The two optical fibers were placed on either side of the same nerve cross section to ensure more uniform IR exposure. A typical sheath thickness is about 100 μm. Since the optical fibers gently touched the nerve sheath, spot size at the nerve surface was 600 μm. The fiber had a numerical aperture of 0.22 (i.e., a beam divergence of 25.4 deg in air), so the spot was slightly larger at the axons due to divergence and scattering. Since the onset response travels both anterogradely and retrogradely from the KHFAC block electrode, applying the lasers to block the onset response near the proximal electrode allowed the distal electrode to serve as a control for the same KHFAC block. Varying placement of the optical fibers between the KHFAC and the distal or proximal recording electrodes had no effect on the results.

Experimental Protocol

Three experiments were performed on three different nerves, using an A-B-A protocol. During protocol A, a train of action potentials was blocked by KHFAC; protocol B added IR inhibition to generate onset response block. Protocol A was repeated as a control. A current just above the stimulation threshold produced CAPs of sufficient amplitude to assess block effectiveness. The minimum amplitude KHFAC waveform at which block was observed was consistently at a frequency of 10 kHz and amplitude ranging from 10 to 15 mA (peak-to-peak). For the two lasers, radiant exposures per pulse ranged from 0.177 to 0.254 J/cm2. Both lasers were switched on at the same time and emitted laser light for 30 s before the KHFAC waveform was applied, using 200-μs pulses at 200 Hz, to allow the temperature to reach a higher value. Nerve health was assessed before and after every experiment by comparing the propagating CAPs traveling down the length of the nerve.

Results

Figure 10:
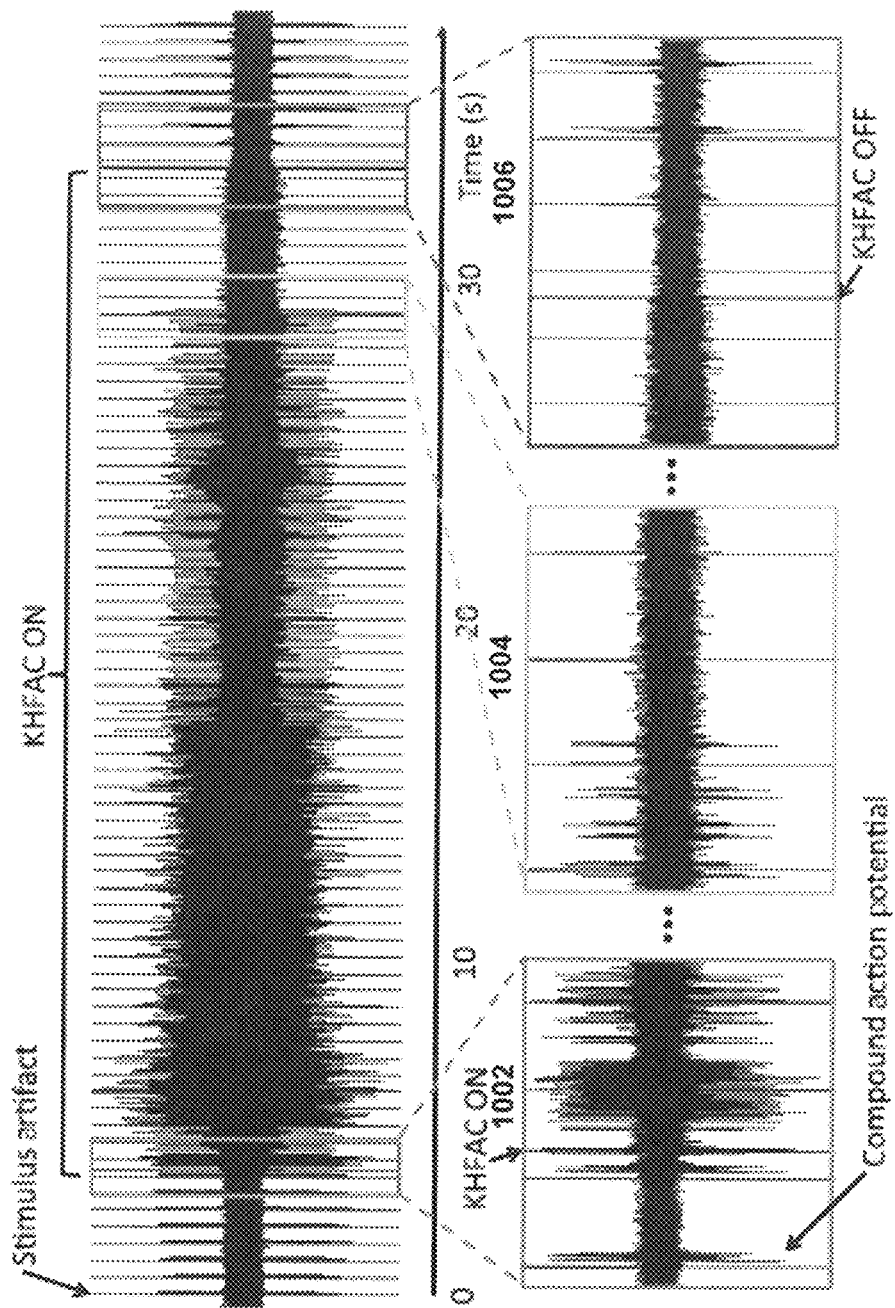
FIG. 10 is an illustration of the onset response seen with KHFAC block as recorded through the distal recording electrode.

FIG. 10 shows that application of KHFAC induced both an onset response (1002), and that it completely blocked the CAP (1004), which returns after KHFAC was turned off (1006).

Figure 11:
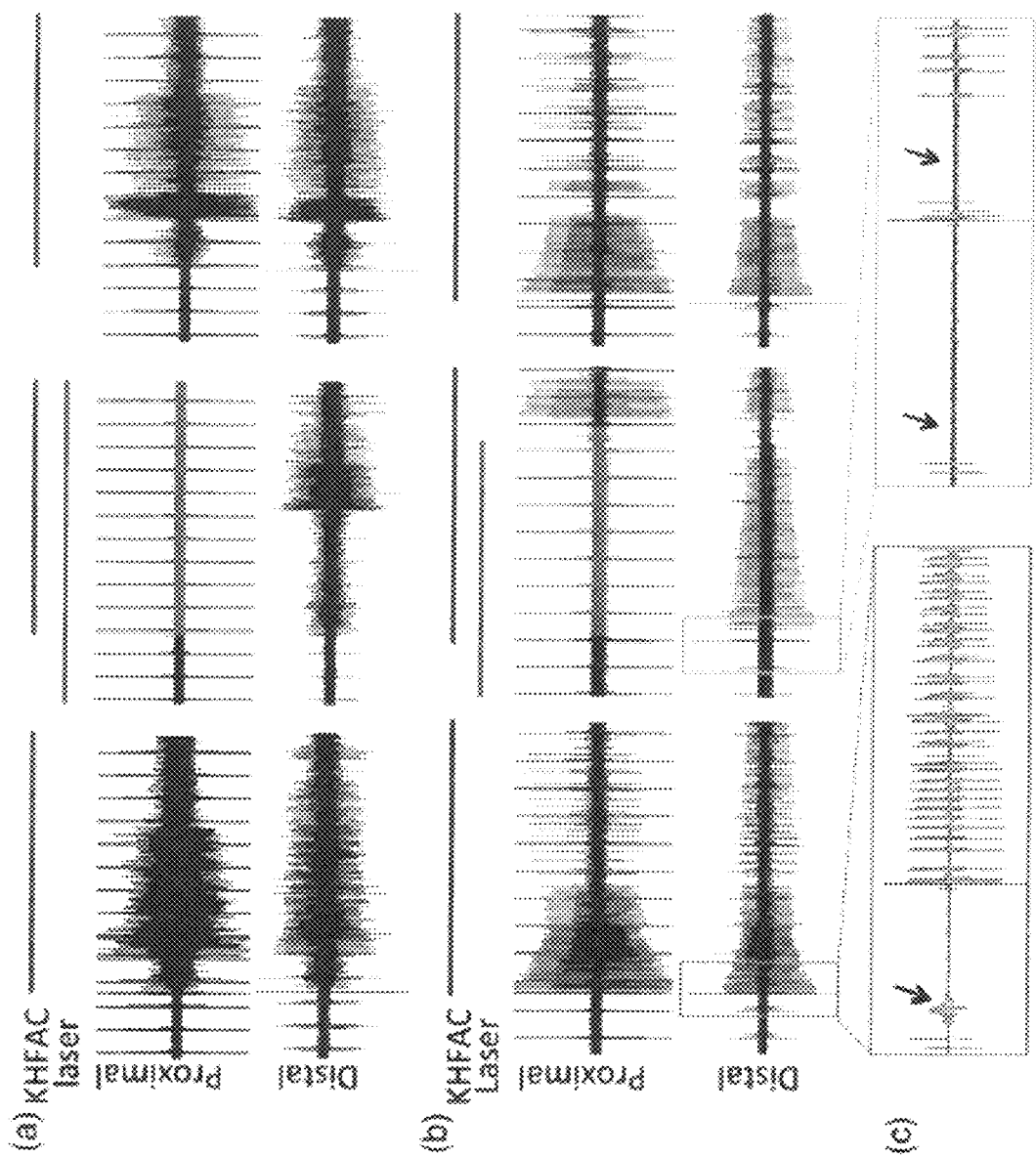
FIG. 11 is an illustration of the onset response seen with KHFAC block and IR block.

When only KHFAC is applied (FIGS. 11(*a*) and 11(*b*), left panels), the onset response is visible in both the proximal and distal recordings. When IR is also applied, the onset response is blocked in the proximal recording only (FIGS. 11(*a*) and 11(*b*), middle panels, shaded rectangles). The onset response was still present at the distal recording because the onset response's propagation to that electrode was unaffected by the laser (FIGS. 9(*d*) and 9(*e*)). Although the onset response was present in the distal recording, the CAP was blocked by the laser (FIG. 11(*c*)). The onset response reappeared proximally as soon as the laser was turned off (FIGS. 11(*a*) and 11(*b*), right panels). After ACIR, CAPs were triggered and had the same amplitude as before ACIR, demonstrating its reversibility. ACIR produced complete onset response block in each experiment (N ¼ 3). The onset response, which has previously been shown to be variable over time, was not identical before, during, and after block, but the block of the onset response was always complete.

From the above description, those skilled in the art will perceive improvements, changes and modifications. For example, in some instances, nerve conduction block according to the systems and methods of the present invention can be used to treat pain or spasticity. Such improvements, changes and modifications are within the skill of one in the art and are intended to be covered by the appended claims.

What is claimed is:

1. A method for blocking conduction in a nerve, comprising:
    applying, by an optrode, a heat signal to the nerve to provide a heat-based nerve block that blocks conduction in the nerve; and
    applying, by an electrode, an electrical signal to the nerve to provide an electrical nerve block to block the conduction in the nerve;
    wherein a timing of the heat signal and another timing of the electrical signal are defined by a control device linked to the optrode and the electrode such that the heat signal and the electrical signal are applied simultaneously for a first period of 1 second or less so that the heat signal blocks an onset response in the nerve generated by the electrical signal, and after the first period of 1 second or less, the heat signal is stopped and the electrical signal is applied alone over a second period of at least one minute after the onset response.

2. The method of claim 1, wherein the heat signal is applied for the first period of 10 milliseconds or less then removed.

3. The method of claim 1, wherein the heat signal is provided to the optrode by at least one of an infrared (IR) light source, a radio frequency (RF) source, an ultrasound (US) source, and an electrical heating source; and
    wherein the electrical signal comprises at least one of a direct current (DC) signal and a kilohertz frequency alternating current (KHFAC) signal.

4. The method of claim 1, wherein the heat signal comprises an IR signal and the electrical signal comprises a KHFAC signal.

5. The method of claim 1, wherein the conduction in the nerve is restored within 1 second or less from removing the electrical signal.

* * * * *

UNITED STATES PATENT AND TRADEMARK OFFICE
CERTIFICATE OF CORRECTION

PATENT NO. : 11,065,467 B2  
APPLICATION NO. : 16/296617  
DATED : July 20, 2021  
INVENTOR(S) : Chiel et al.

Page 1 of 1

It is certified that error appears in the above-identified patent and that said Letters Patent is hereby corrected as shown below:

On the Title Page

Item (71), Applicant:
Add --Vanderbilt University Nashville, TN (US)-- as the second applicant.

Signed and Sealed this
Twenty-first Day of December, 2021

Drew Hirshfeld
*Performing the Functions and Duties of the*
*Under Secretary of Commerce for Intellectual Property and*
*Director of the United States Patent and Trademark Office*